United States Patent [19]

Heacock et al.

[11] Patent Number: 4,728,183

[45] Date of Patent: Mar. 1, 1988

[54] OPHTHALMIC LENS FOR OBSERVING THE FUNDUS OF THE EYE

[75] Inventors: Gregory L. Heacock, Bellevue, Wash.; Martin A. Mainster, Lenexa, Kans.; Phillip J. Erickson, Kirkland, Wash.

[73] Assignee: Ocular Instruments, Inc., Bellevue, Wash.

[21] Appl. No.: 914,007

[22] Filed: Oct. 1, 1986

[51] Int. Cl.⁴ .................. A61B 3/10; G02B 3/04; G02C 7/04

[52] U.S. Cl. .................... 351/219; 350/432; 351/160 R; 351/205

[58] Field of Search ............. 351/160 R, 160 H, 161, 351/162, 219, 205; 350/415, 432

[56] References Cited

U.S. PATENT DOCUMENTS

| | | | |
|---|---|---|---|
| 3,954,329 | 5/1976 | Pomerantzeff | 351/219 |
| 4,134,647 | 1/1979 | Ramos-Caldera | 351/219 |
| 4,410,245 | 10/1983 | Koester | 351/219 |
| 4,469,413 | 9/1984 | Shirayanagi | 350/432 |

FOREIGN PATENT DOCUMENTS

| | | | |
|---|---|---|---|
| 124502 | 5/1984 | European Pat. Off. | 351/219 |
| 2246182 | 3/1974 | Fed. Rep. of Germany | 351/219 |
| 2660505C2 | 9/1977 | Fed. Rep. of Germany | 351/219 |
| 2248814 | 5/1975 | France | 351/219 |

OTHER PUBLICATIONS

P. Roussel et al., "Contact Glass for Use . . . Optical Aspects", International Ophthalmology 6: 183–190 (1983).

Primary Examiner—John K. Corbin
Assistant Examiner—Scott J. Sugarman
Attorney, Agent, or Firm—Christensen, O'Connor, Johnson & Kindness

[57] ABSTRACT

An ophthalmic lens utilized for observing the fundus of an eye using through the lens illumination and for delivering a focused laser beam to the fundus includes a contact lens and an aspheric entry lens. In combination, the lenses provide an aerial image of the fundus anterior to the entry lens.

9 Claims, 1 Drawing Figure

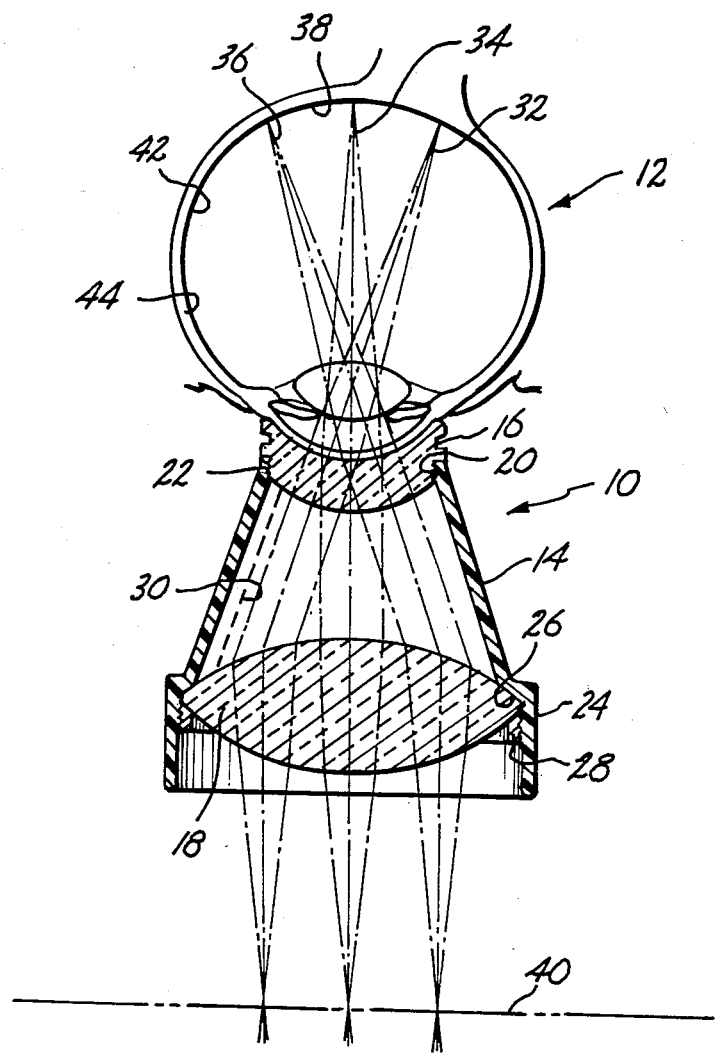

OPHTHALMIC LENS FOR OBSERVING THE FUNDUS OF THE EYE

TECHNICAL BACKGROUND

The present invention relates to ophthalmic lenses employed in connection with ophthalmic diagnostic and surgical procedures, and more particularly to a compound ophthalmic lens that is utilized for observation of the fundus and for delivery of a laser beam to the fundus.

Ophthalmic lenses are conventionally utilized for observation of various locations within the eye by ophthalmologists. These ophthalmic lenses normally include a contact lens, that is a lens that directly contacts the cornea of the eye, and an entry lens that is spaced in the anterior direction from the contact lens. The objective lens usually magnifies that portion of the eye being observed. The two lenses are normally joined by a housing. Mirrors are sometimes interposed between the contact lens and the entry lens to increase the field that can be viewed by the physician through the lens.

Most ophthalmic lenses of the type just described have been created and designed for use as an observation tool utilized in conjunction with a slit lamp or ophthalmic microscope employed by ophthalmologists. While most prior lenses function reasonably well for use as an observation tool, the advent of laser microsurgery and the accompanying need to deliver a laser beam safely within the eye has created a need for ophthalmic lenses that not only provide improved images of the desired location in the eye, but also have the capability to deliver laser energy to the desired location with minimum effect on other portions of the eye.

One example of the use of laser energy is in connection with the treatment of a patient's fundus. This treatment requires not only the capability to observe the fundus over a wide angle but the capability of being able to deliver a laser beam within the eye and focus it on the fundus. The only lens currently available for wide field fundus observation has at least three elements. The lens forms a real image within the final lens element. While the fundus image so created is adequate, axial magnification is poor, and the internal and external reflections caused by the various lens elements degrades the overall image available and reduces fundus detail if the ocular media is hazy. Moreover, the prior lens exhibits aberrations around the peripheral portion of the image and laser delivery to the peripheral retina is adversely affected by beam astigmatism induced by the lens. Of even more concern is the small beam diameter produced by the prior lens at the level of the cornea and crystalline lens. This small beam diameter has been shown to be potentially hazardous to these structures.

SUMMARY OF THE INVENTION

The present invention provides an improved lens that not only offers a greatly improved image for the physician, but also minimizes the adverse effects upon the cornea and crystalline lens. The lens constructed in accordance with the present invention includes a contact lens, an entry lens and a holder means for interconnecting and fixing the lenses relative to each other. The contact lens has a posterior surface and an anterior surface. The posterior surface has a radius of curvature substantially the same as the anterior surface of the average cornea. The anterior surface of the contact lens has a radius of curvature that is configured so that the light rays emerging from the patient's eye through the crystalline lens and cornea are rendered substantially parallel as the exit from the anterior surface of the contact lens. The entry lens is positioned anterior to the contact lens and is coincident with the optical axis of the contact lens. The entry lens is aspheric, having both posterior and anterior surfaces. The aspheric lens is spaced from the contact lens and the posterior and anterior surfaces of the entry lens are constructed so as to collect the parallel light rays emerging from the contact lens and produce a substantially planar aerial image anterior to and in close proximity to the aspheric lens.

A lens constructed in accordance with the present invention has several advantages over prior lenses. First, the lens of the present invention has fewer optical elements, producing a very light efficient, high resolution system. The small number of optical elements also produce very little reflected and scattered light, allowing the physician to employ through the lens illumination and eliminating the need for a scleral transilluminator or other means of fiberoptic illumination. The simple optical path provided by the lens of the present invention provides a high resolution image as well as a nondistorting path through which a laser beam can pass during treatment of a patient's pathology. Moreover, light rays emerging from the patient's eye through the lens constructed in accordance with the present invention are parallel until collected and focused by the aspheric lens element. This parallel light section ensures that the laser energy passing through the patient's cornea and crystalline lens will be passing through the largest possible area before it is finally focused on the pathology by the power of the contact lens, the patient's cornea and the crystalline lens. In addition, a lens constructed in accordance with the present invention develops the image of the patient's fundus in air, not in the optical element as with the prior art lens. This capability again provides a sharp ophthalmoscopic image that can easily be viewed through a conventional ophthalmic microscope and, moreover, provides a location exterior to the ophthalmic lens on which a laser can be focused for delivery to the patient's eye.

BRIEF DESCRIPTION OF THE DRAWINGS

A better understanding of the present invention can be derived by reading the ensuing specification in conjunction with the accompanying drawing wherein the FIGURE is a schematic view of the lens constructed in accordance with the present invention shown positioned on a patient's eye.

DETAILED DESCRIPTION OF THE INVENTION

Referring first to the FIGURE, a contact lens, generally designated 10, is positioned adjacent to the eye of a patient, which is shown in cross section and generally designated 12. The contact lens 10 includes a generally frustoconically-shaped housing 14, which serves both as a device by which the optical elements are positioned in space relative to each other and as a device by which the ophthalmic lens can be manipulated. A contact lens 16 is affixed to the smaller diameter end of the housing 14 while an aspheric entry lens 18 is fixed to the larger diameter end of the housing 14. The contact lens 16 is preferably composed of an optically transparent, inert polymeric material such as polymethylmethacrylate, or other suitable optically transparent material. It is preferred on the other hand that the aspheric lens be composed of a high quality optical glass. The smaller diameter portion of the housing 14 has internal threads 20 that engage external threads 22 to affix the contact lens 16 to the housing 14. The anterior end of the housing 14 comprises a cylindrical shell 24. The diameter of the cylindrical shell is slightly greater than the larger diameter portion of the frustoconical section of the housing 14. The frustoconical section of the housing is joined to the cylindrical shell 24 by a shoulder 26 that has an outwardly facing surface. The periphery of the outwardly facing shoulder 26 receives the outer edge of the aspheric lens 18 to thus fix the distance by which the apsheric lens 18 is spaced from the contact lens 16. The interior of the cylindrical shell 24 is threaded and receives an externally threaded retaining ring 28, which is screwed down to secure the aspheric lens against the shoulder 26.

Still referring to the FIGURE, the three bundles of light rays 32, 34 and 36 illustrate the desirable optical characteristics of the lens. The light rays 32, 34, and 36 are shown originating at the fundus 38 of the eye 12. The rays diverge from the fundus and are converted to a parallel bundle by the contact lens 16. The aspheric lens constructed in accordance with the present invention then focuses those rays in a flat focal or image plane indicated by dot dash line 40 at a position anterior to the aspheric lens. Thus, any portion of the fundus images can readily be observed in the focal plane. Moreover, when the lens is used for laser delivery, the parallel nature of the rays between the two lenses will yield the widest possible laser beam as it passes through the cornea and crystalline lens, thus, miminizing the risk to those elements of the eye.

The posterior surface of the contact lens 16 has a radius of curvature that is substantially the same as the radius of curvature of the average cornea. A radius of curvature of 7.45 mm is preferred for a lens constructed in accordance with the present invention. The radius of curvature of the anterior surface of the contact lens can range of from 7 mm to 15 mm, and most preferably is 9.5 mm. The thickness of the contact lens along the optical axis can be on the order of from 1 mm to 12 mm and is most preferably 5 mm in thickness. While the diameter of the contact lens can be varied, the diameter of the optical portion of the lens is most preferably on the order of 12.5 mm, while the diameter of the anterior surface is preferably on the order of 14.2 mm to achieve a wide angle of view. The housing 14 is designed so that the distance between the aspheric lens and the contact lens along the optical axis is preferably 10 mm. However the distance can be varied from 0 mm to 25 mm without departing from the overall concepts of the present invention.

The shape of the aspheric lens is very important in achieving the desired results for a lens constructed in accordance with the present invention. Both the anterior and posterior surfaces of the aspheric lens can be defined by the formula:

$$Z = \frac{CK^2}{1 + \sqrt{1 - C^2 E K^2}}$$

wherein $C = (1/R)$, $E = b + 1$, and $K^2 = x^2 + y^2$.

For the anterior surface of the aspheric lens, R can range from 14 mm to 50 mm, and preferably is 19.8 mm. For the anterior surface, b can range from $-54$ to $-4$, and preferably is about $-9.7$. For the posterior surface of the lens, R can range from 10 mm to 25 mm, and preferably is about 17 mm. For the posterior surface, b can range from about $-0.6$ to $-2$, and preferably is about $-0.7$. The sign convention for foregoing formula $+Z$ extends in the posterior direction. The thickness of the aspheric lens along the optical axis can range from 8.5 mm to 16.5 mm, and is preferably 12.4 mm. A most preferred diameter for the aspheric lens is about 30 mm.

For vitreo-retinal surgical applications, for example for vitrectomy, a miniaturized version of a lens constructed in accordance with the present invention is preferred. The preferred materials for this invention are chosen so that they can withstand autoclaving temperatures without degradation. The optical principles employed are the same, but the lens is preferably reduced in size to allow the surgeon to manipulate surgical instruments within the eye without interference by the physical presence of the lens.

The contact lens of the miniaturized version can be constructed in accordance with the same parameters as set forth for the full size lens. For the contact lens, the radius of curvature of the anterior surface can range from 7 mm to 15 mm, with 9.0 mm being preferred. The thickness of the contact lens can range from 1 mm to 12 mm, with 6.0 mm being preferred. The diameter of the optical zone is preferably 11.4 mm, while the diameter of the anterior surface is preferably 14.1 mm. The housing of the miniaturized version of the lens can be constructed so that the distance between the lenses can vary from 0 mm to 15 mm, while a separation of 2 mm is preferred. For the anterior surface of the aspheric lens, R can range from 10 mm to 100 mm, and preferably is 21.6 mm. For the anterior surface, b can range from $-900$ to $-7$, and preferably is about $-33.6$. For the posterior surface of the lens, R can range from 6.5 mm to 11 mm, and preferably is about 7.6 mm. For the posterior surface, b can range from about $-0.54$ to $-1.08$, and preferably is about $-0.63$. The thickness of the aspheric lens along the optical axis can range from 4 mm to 13 mm, and is preferably 8.8 mm. A most preferred diameter for the lens is about 18 mm. For both the regular and miniaturized versions of the lenses, it is preferred that the dioptic power of the anterior surface is less than one and one-half times the dioptic power of the posterior surface at the vertex of each surface.

Still referring to the FIGURE, the three bundles of light rays 32, 34 and 36 illustrate the desirable optical characteristics of the lens. The light rays 32, 34, and 36 are shown originating at the fundus 38 of the eye 12. The rays diverge from the fundus and are converted to a parallel bundle by the contact lens 16. The aspheric lens constructed in accordance with present invention then focuses those rays in a substantially planar focal or image plane indicated by dot dash line 40 at a position anterior to the aspheric lens. Thus, any portion of the fundus image can readily be observed in the focal plane. Moreover, when the lens is used for laser delivery, the parallel nature of the rays between the two lenses will yield a wide laser beam diameter as it passes through the cornea and crystalline lens, thus, minimizing the risk to those elements of the eye.

An alternate embodiment of the present invention employs a planar mirror positioned perpendicular to the plane of the drawing along the dot dash line 30 shown in the FIGURE. The planar mirror is positioned between the contact lens and the aspheric lens. This structure allows the ophthalmologist using the ophthalmic lens to readily observe the equatorial and even the far peripheral portions of the eye, which otherwise would require a significant movement of the contact lens or might be impossible.

In addition to the advantages already discussed, a lens constructed in accordance with the present invention can be produced in a smaller overall diameter than prior ophthalmic lenses, and thus can easily be hand held. Additionally, the very flat focal plane at which the real image is produced insures that the entire image will be in focus when viewed with an ophthalmic microscope, thus eliminating distortions in the peripheral regions of the image. Additionally, the very flat focal plane allows near perfect laser transmission and focusing even at the extremities of the lens.

In summary, the present invention provides a lens that produces a bright, sharply focused, high resolution, illumination efficient fundus image that is nearly reflection free. Moreover, the very flat nature of the image plane allows precise laser delivery to virtually any portion of the fundus that can be seen in the image plane.

While the present invention has been described in conjunction with the preferred embodiment and the variations thereof, one of ordinary skill after reviewing the foregoing specification will be able to effect various changes, substitutions of equivalents and other alterations without departing from the broad concepts disclosed herein. It is therefore intended that letters patent granted hereon be limited only by the definition contained in the appended claims and equivalents thereof.

The embodiments of the invention in which an exclusive property or privilege is claimed are defined as follows:

1. An ophthalmic lens for observing the fundus of the eye comprising:
    a contact lens having a posterior surface and an anterior surface, said posterior surface having a radius of curvature substantially the same as the anterior surface of a cornea, the anterior surface of the contact lens having a radius of curvature such that the light rays emerging from the patient's eye through the crystalline lens and cornea are substantially parallel as they exit in an anterior direction from the contact lens,
    an entry lens positioned anterior to the contact lens, the optical axis of the contact lens and said entry lens being substantially coincident, said entry lens being aspheric, the posterior and anterior surfaces of said entry lens being constructed and said entry lens being spaced from said contact lens so as to collect said parallel light rays emerging from the contact lens and produce an aerial image anterior to and in close proximity to the entry lens, the surfaces of said entry lens being defined by the formula:

$$Z = \frac{CK^2}{1 + \sqrt{1 - C^2 E K^2}},$$

wherein $C = (1/R)$, $E = b + 1$, and $K^2 = x^2 + y^2$, wherein for the anterior surface of the lens R ranges from 14 mm to 50 mm and b ranges from $-54$ to $-4$, and wherein the posterior surface of said lens, R ranges from 10 mm to 25 mm and b ranges from $-0.6$ to $-2$, and holder means for interconnecting and fixing said lenses relative to each other.

2. The ophthalmic lens of claim 1 further comprising:
    a mirror positioned between said contact lens and said entry lens at an angle such that the equator and far periphery of the eye can be observed in the plane of said aerial image.

3. The ophthalmic lens of claim 1 wherein for the anterior surface R is about 19.8 mm and b is about $-9.7$, and for the posterior surface, R is about 17 mm and b is about $-0.7$.

4. The ophthalmic lens of claim 1 wherein the radius of curvature of the anterior surface of the contact lens ranges from about 7 mm to about 15 mm.

5. The ophthalmic lens of claim 4 wherein the radius of curvature for the anterior surface is about 9.5 mm.

6. An ophthalmic lens for observing the fundus of the eye comprising:
    a contact lens having a posterior surface and an anterior surface, said posterior surface having a radius of curvature substantially the same as the anterior surface of a cornea, the anterior surface of the contact lens having a radius of curvature such that the light rays emerging from the patient's eye through the crystalline lens and cornea are substantially parallel as they exit in an anterior direction from the contact lens,
    an entry lens positioned anterior to the contact lens, the optical axis of the contact lens and said entry lens being substantially coincident, said entry lens being aspheric, the posterior and anterior surfaces of said entry lens being constructed and said entry lens being spaced from said contact lens so as to collect said parallel light rays emerging from the contact lens and produce an aerial image anterior to and in close proximity to the entry lens, the surfaces of said entry lens being defined by the formula:

$$Z = \frac{CK^2}{1 + \sqrt{1 - C^2 E K^2}},$$

wherein $C = (1/R)$, $E = b + 1$, and $$K^2 = x^2 + y^2,$$

wherein for the anterior surface of the lens R ranges from 10 mm to 100 mm and b ranges from −900 to −7, and wherein for the posterior surface of said lens, R ranges from 6.5 mm to 11 mm and b ranges from −0.54 to −1.08, and holder means for interconnecting and fixing said lenses relative to each other.

7. The ophthalmic lens of claim 6 wherein for the anterior surface R is about 21.6 mm and b is about −33.6, and for the posterior surface, R is about 7.6 mm and b is about −0.63.

8. The ophthalmic lens of claim 6 wherein the radius of curvature of the anterior surface of the contact lens ranges from about 7 mm to about 15 mm.

9. The ophthalmic lens of claim 8 wherein the radius of curvature for the anterior surface is about 9.0 mm.

* * * * *